United States Patent [19]

Andersen

[11] 4,354,496
[45] Oct. 19, 1982

[54] HOOD FOR PREVENTION OF SCALP HAIR LOSS

[76] Inventor: Esther Andersen, 1735 N. Green Bay Rd., Racine, Wis. 53405

[21] Appl. No.: 244,681

[22] Filed: Mar. 17, 1981

[51] Int. Cl.³ .............................................. A61F 7/00
[52] U.S. Cl. ..................................... 128/403; 128/399
[58] Field of Search .................................. 128/399–403

[56] References Cited

U.S. PATENT DOCUMENTS

| | | | |
|---|---|---|---|
| 1,473,506 | 11/1923 | Nessler | 128/403 |
| 1,549,510 | 8/1925 | Schnitzler | 128/403 |
| 2,116,009 | 5/1938 | Brown | 128/403 |
| 2,416,788 | 3/1947 | Andrews | 128/402 |
| 3,090,045 | 5/1963 | Hurst | 128/403 |
| 3,465,161 | 8/1969 | Andrassy | 128/402 |
| 3,587,577 | 6/1971 | Smirnov et al. | 128/402 |
| 3,696,814 | 10/1972 | Umemoto | 128/402 |
| 4,172,495 | 10/1979 | Zebuhr et al. | 128/402 |

Primary Examiner—Kyle L. Howell
Assistant Examiner—C. W. Shedd
Attorney, Agent, or Firm—Darby & Darby

[57] ABSTRACT

A hypothermic scalp tourniquet hood comprises an exterior flexible elongated casing and interior flexible elongated casing. The two casings are joined at their bottom. The interior casing is closed at the top and the exterior casing is open to form a space in which ice can be placed. A drawstring is positioned within the hood at the bottom so that tourniquet-like pressure can be applied to the hairline of the user when the hood is in place.

5 Claims, 4 Drawing Figures

HOOD FOR PREVENTION OF SCALP HAIR LOSS

BACKGROUND OF THE INVENTION

This invention relates generally to a combination coolant hood and scalp tourniquet for the prevention of scalp hair loss.

It is known that people afflicted with various forms of cancer may be treated by chemotherapy. A chemical agent placed into the patient's bloodstream is transported to the cells of the body. The uptake of the chemical by the cells in the scalp may have an adverse effect on the functioning of the hair follicles and result in hair loss. While hair loss may be considered primarily to be a minor cosmetic complication, the negative psychological impact on the patient may seriously impede the success of the treatment.

Hair shafts are rooted in hair follicles in the dermis. The hair follicle is a tubular epithelial or membranous cellular tissue which surrounds the lower part of the hair shaft. At the bottom of the follicle is a vascular papilla which supplies the growing basal part of the hair with nourishment. The rate and quantity of the chemotherapeutic agent accepted by hair follicle cells can be reduced if the blood vessels in the papilla are contricted. Constriction of the blood vessels, known as vasoconstriction, can be accomplished by applying physical pressure to the vessels and by subjecting the vessels to temperatures below normal body temperature. The application of pressure with a compress, tightly fastened bandage, or tourniquet, is a well-known method for reducing bleeding by pressure vasoconstrictuion. However, prolonged application of high pressure may permanently damage blood vessels, blocking the flow of blood to the affected area when the pressure is reduced. The application of a tourniquet to the scalp at a sufficiently high pressure to reduce blood flow to the scalp during chemotherapy, and thereby reduce the follicle cell uptake of the chemotherapeutic agent, has been found to be unsatisfactory when used by itself in minimizing or preventing scalp hair loss.

A number of devices are known for inducing vasoconstriction by subjecting the body to subnormal temperatures. This type of vasoconstriction is known as hypothermia. Owens U.S. Pat. No. 1,569,877 discloses a tubular container lined with a waterproof material. The tubular device has a plurality of compartments capable of being filled with ice. The tubular container is tied closed after filling the compartments and then wrapped around the selected body area. Williamson U.S. Pat. No. 1,964,655 also discloses a body cooling device with a single coolant compartment connected to an elastic band having two openings and a belt buckle arrangement. The patient's ears are placed within the openings and the elastic band is buckled to keep the device fixed in its desired location. Henderson U.S. Pat. No. 4,204,543 also discloses a collant bank of elasticized soft textile material with at least one compartment having a pouch for the insertion of individual removable collant containers. Burns U.S. Pat. No. 1,169,123 discloses a head band with a plurality of hot water bottles for alignment with preselected locations around the patient's forehead. The bottles are held in place by strings which also act to adjust the length of the bank and for attachment of a skull icecap.

Other scalp cooling devices are also known. One such device contains compartments permanently enclosing a freezable liquid. The entire device is refrigerated before it is applied to the patient. Another device which is especially designed for scalp hypothermia is constructed of paper. It contains a plurality of compartments containing water and a chemical such as ammonium nitrate. When the compartments are ruptured a cooling gel is produced which remains cool for about 30 to 45 minutes. The device cannot be reused after the compartments are ruptured and the cooling life of the gel may not be suitable for the duration of one treatment. Application of the device to the scalp is time-consuming and difficult. Furthermore, the device must be kept in place during treatment by wrapping an elastic bandage around the device and taping the bandage to keep it from unraveling. The device attempts to reduce hair loss resulting from chemotherapy by means of hypothermic vasoconstriction only. There is no pressure vasoconstriction of the blood vessels in the scalp.

OBJECTS OF THE INVENTION

The main object of the present invention is to provide an improved device for preventing hair loss resulting from chemotherapy.

A more specific object of the invention is to provide a combination coolant hood and tourniquet for the prevention of hair loss resulting from chemotherapy which is simple to use and capable of being reused.

SUMMARY OF THE INVENTION

Briefly, in accordance with the invention, a hypothemic tourniquet hood for preventing hair loss during chemotherapy, comprises an open exterior flexible casing connected at its bottom edge to an interior flexible casing so that a space is formed between the two casings into which ice may be placed. A drawstring is located at the bottom of the joined casing so that when the casing is applied to the patient's head, the drawstring can be drawn tightly around the patient's hairline as a tourniquet to reduce blood flow to the scalp.

In a preferred embodiment, the space between the two casings is divided into a plurality of compartments by appropriately located partitions and the top of the hood is closed by a second drawstring or the like.

THE DRAWING

DETAILED DESCRIPTION

Figure 1:
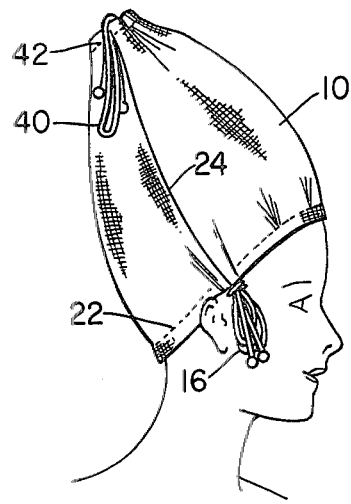
FIG. 1 is a perspective view of a hood in accordance with the invention in place on a user.
Figure 2:
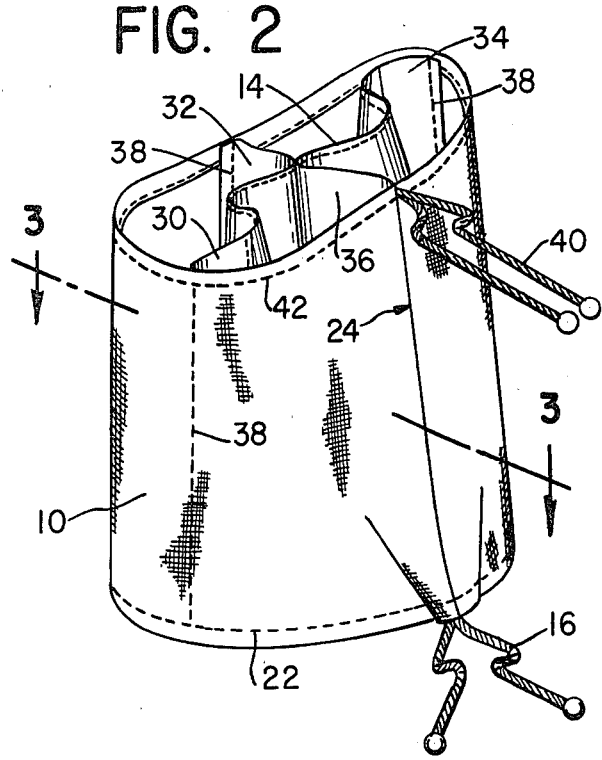
FIG. 2 is a perspective view of the hood in its open position before ice is placed within its compartments.
Figure 3:
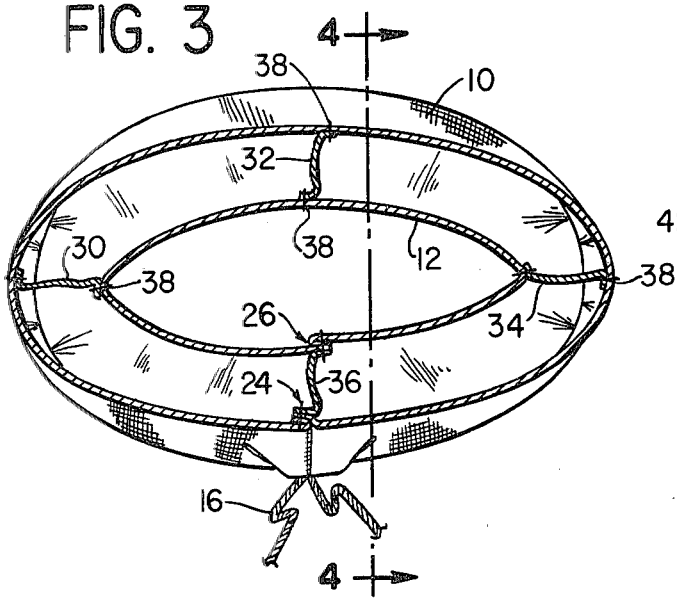
FIG. 3 is a sectional view along the line 3—3 of FIG. 2.
Figure 4:
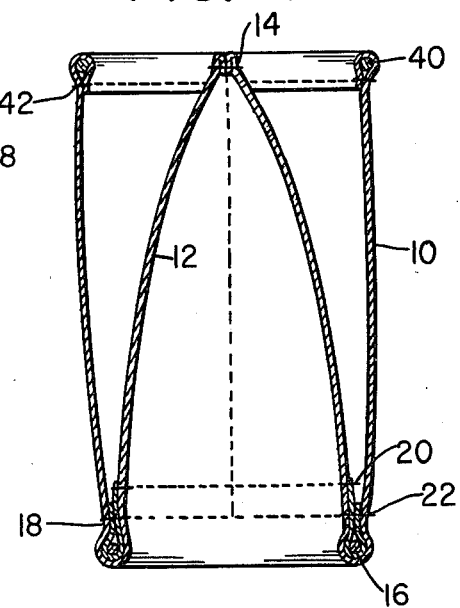
FIG. 4 is a sectional view along the line 4—4 of FIG. 3.

The construction of the hood according to the invention is shown in FIGS. 2, 3 and 4. Essentially, the hood includes an exterior elongated casing 10 and an interior elongated casing 12. The two casings are joined at the bottom, and the exterior casing 10 is open at the top so that a space is formed between the exterior and interior casings. In a preferred embodiment, the top of the interior casing 12 is closed by a seam 14 so that the patient's head will be protected from the ice or other coolant placed in the spaced formed between the exterior and interior casings 10 and 12, respectively.

In accordance with a principle feature of the invention, a drawstring 16 is located at the bottom of the hood where the two casings 10 and 12 are joined. The drawstring 16 may be situated in a pocket formed by a narrow fabric strip 18 folded and positioned between the bottom extremities of casings 10 and 12 (FIG. 4). A circumferential seam 20 fastens one edge of the fabric strip 18 to interior casing 12 and a parallel, lower seam 22 fastens the two casings 10 and 12 about the strip 18 and drawstring 16.

The specific construction of the casings is not a feature of the invention. In one embodiment, the two casings are formed of a single piece of fabric folded upwardly (FIG. 4) with the elongated (longitudinal) edges of casings 10 and 12 joined as shown at 24 and 26, respectively, in FIG. 3.

In the preferred embodiment, four flexible partitions 30, 32, 34 and 36 are sewn longitudinally between the exterior and interior casings 10 and 12 as shown in FIG. 3. These barrier panels may be sewn in place along seams 38 and divide the space between casings 10 and 12 into four circumferential compartments of approximately equal size.

The top of the exterior casing is folded on itself to receive a second upper drawstring 40 which is retained in place as by seam 42. After the hood has been placed on the user's head and ice placed in the compartments defined by the partitions 30, 32, 34 and 36, between the exterior and interior casings 10 and 12, the upper drawstring 40 may be pulled and tied.

The material of which the hood is made should be waterproof so that the melting ice will not leak. Obviously, it must be able to transfer heat from the user's scalp to the ice within the space between the two casings.

In accordance with the invention, the hood is advantageously used by placing the hood on the patient's head such that the lower drawstring 16 is just above the patient's ears at the hairline. The string is then pulled tight and tied to apply a tourniquet-like pressure to the scalp. The open compartments (between casings 10 and 12) are then filled with crushed ice and the ice is positioned so that the entire scalp is in close contact with the coolant. The upper cord 40 is then tied to secure the hood in place. The separate compartments formed by the partitions 30, 32, 34 and 36 help to maintain the ice in contact with the entire scalp during use.

Advantageously, the chemotherapy treatment should not start until about fifteen minutes after the hood has been applied. After the treatment has been completed, the hood should remain in place on the patient's head for at least twenty minutes before removal. The device is readily removed from the patient's head by releasing the lower drawstring 16 and lifting at the top. Drawstring 40 may then be released and the ice removed, after which the hood can be reused.

What is claimed is:

1. A hypothermic tourniquet hood to prevent scalp hair loss comprising,
   an exterior flexible elongated casing open at the top and bottom, the bottom adapted to be placed on the head of a user,
   an interior flexible elongated casing within said exterior casing, said interior casing being closed at its top end and joined to said exterior casing at its bottom to form a space between said casings which can be filled with ice, and
   a drawstring around the bottom of the joined casings, the diameter and position of said drawstring being such that it can be drawn tight to apply pressure as a tourniquet to a patient's hairline.

2. A hypothermic scalp tourniquet hood according to claim 1, including a plurality of partitions between said casings to divide said space into separate compartments.

3. A hypothermic scalp tourniquet hood according to either of claims 1 or 2, wherein a second drawstring is positioned around the top of the exterior casing to close the space between the casings after it has been filled with ice.

4. A hypothermic scalp tourniquet hood according to claim 2, wherein the partitions are attached between the inner casing and the exterior casing.

5. A hypothermic scalp tourniquet hood, comprising,
   an exterior elongated flexible casing open at the top and bottom, the bottom adapted to be placed on the head of a user,
   an interior elongated, flexible casing within said exterior casing, said interior casing being substantially the same length as the exterior casing and closed at its top, the bottom edges of said casings being joined to form a space between said casings which can be filled with ice,
   a plurality of partitions between said casings to divide said space into separate circumferential compartments, said partitions being sewn to said exterior and interior casings along substantially their entire lengths between said top and said bottom,
   a drawstring around the bottom of the joined casings, the diameter and position of said drawstring being such that it can be drawn tight to apply pressure as a tourniquet to a patient's hairline, and
   a drawstring at the top of the hood for closing said compartments after they have been at least partially filled with ice.

* * * * *